United States Patent

Ringold et al.

Patent Number: 4,457,941
Date of Patent: Jul. 3, 1984

[54] USE OF PYRROLO-PYRROLE IN TREATING MICROVASCULAR DISEASES ASSOCIATED WITH DIABETES

[75] Inventors: Howard J. Ringold, Woodside; S. David Waterbury, San Mateo, both of Calif.

[73] Assignee: Syntex (U.S.A.) Inc., Palo Alto, Calif.

[21] Appl. No.: 360,753

[22] Filed: Mar. 22, 1982

[51] Int. Cl.³ .............................................. A61K 31/40
[52] U.S. Cl. ..................................................... 424/274
[58] Field of Search ......................................... 424/274

[56] References Cited

U.S. PATENT DOCUMENTS

| | | | |
|---|---|---|---|
| 4,087,539 | 5/1978 | Muchowski et al. | 424/274 |
| 4,089,969 | 5/1978 | Muchowski et al. | 424/274 |
| 4,097,579 | 6/1978 | Muchowski et al. | 424/274 |
| 4,140,698 | 2/1979 | Van Horn et al. | 424/274 |
| 4,232,038 | 11/1980 | Kluge et al. | 424/274 |
| 4,344,943 | 8/1982 | Muchowski et al. | 424/274 |

Primary Examiner—Douglas W. Robinson
Attorney, Agent, or Firm—Hana Dolezalova; Tom M. Moran; Alan M. Krubiner

[57] ABSTRACT

The present invention concerns a new use of certain pyrrolo-pyrrole compounds of chemical formulas (A), (B), (C), and (D):

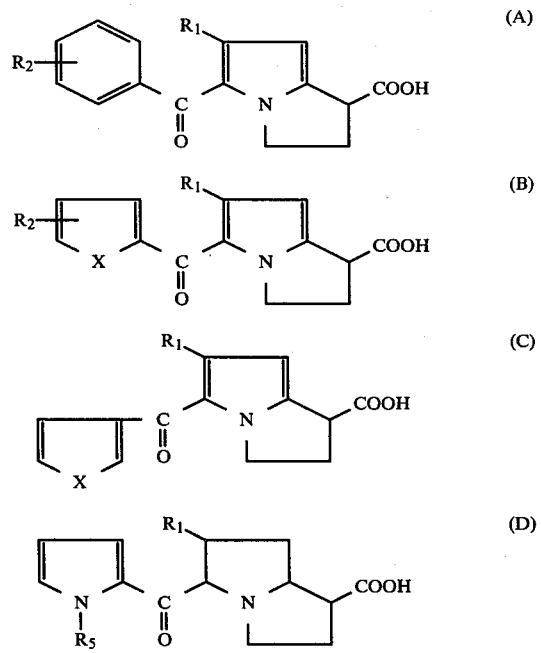

for the treatment of microvascular complications associated with diabetes such as, for example, diabetic retinopathy, diabetic nephropathy and diabetic neuropathy. Pyrrolo-pyrrole compounds prevent development, restrain further progress and relieve symptoms of already developed microvascular complications of diabetes.

10 Claims, No Drawings

USE OF PYRROLO-PYRROLE IN TREATING MICROVASCULAR DISEASES ASSOCIATED WITH DIABETES

BACKGROUND OF THE INVENTION

1. Field of the Invention

This invention relates to a new method for the treatment of microvascular complications associated with diabetes mellitus in mammals, particularly to those microvascular diseases associated with the vascular system of the retina, kidney, nerves and skin such as diabetic retinopathy, diabetic nephropathy and diabetic neuropathy.

2. Related Disclosures

A class of pyrrolo-pyrrole compounds have now been found to be useful in the treatment of microvascular diseases associated with diabetes mellitus. The same compounds were previously known to be useful as antiinflammatories, analgesics, antipyretics and as smooth muscle relaxants. U.S. Pat. Nos. 4,232,038; 4,097,579; 4,087,539 and 4,089,969.

Diabetes mellitus is a disease resulting from a variable interaction of hereditary and environmental factors characterized by abnormal insulin secretion and a variety of metabolic and vascular manifestations reflected in a tendency toward inappropriately elevated blood glucose, thickening of capillary basal lamina, accelerated non-specific atherosclerosis, and neuropathy. Complete clinical syndrome of diabetes mellitus involves hyperglycemia, large vessel disease, microvascular disease and neuropathy.

Microangiopathies are pathological processes affecting the walls of the capillaries, the precapillary arteriols and post capillary venules. They may cause altered local blood flow, progressive reversible dilation of small veins, periodic arteriolar vessel constriction, sclerosis of the walls of arteriols, small veins and capillaries, and slowly progressing microcirculatory decompensation. The basement membranes of the attached capillaries and terminal arteriols are frequently thickening. *The Merck Manual,* 13th edition, 1289, (1977).

Diabetic retinopathy, one of the most pronounced complications of diabetes is a fair representative of microvascular diseases associated with diabetes. The degree of diabetic retinopathy is related to the duration. Compounds of this invention have been found useful in treating diabetic retinopathy and other microvascular complications associated with diabetes such as, for example, diabetic nephropathy or diabetic neuropathy. The effect of pyrrolo-pyrrole compounds on the microvascular diseases associated with diabetes is severalfold. Among others, the drugs prevent neovascularization, prevent leakage of macromolecules from the vessel and affect permeability of the vessel to prevent vasculary edema. Although their usefulness as anti-inflammatories, analgesics, muscle relaxants, and antipyretics, have been previously known, it is surprising to find that these compounds also result in a prevention, inhibition or regression of microvascular diseases in mammals.

SUMMARY OF THE INVENTION

This invention is a new method for treating, inhibiting and preventing microvascular diseases associated with diabetes mellitus in mammals, which method comprises administering to a mammal in need thereof, a therapeutically affective amount of a pyrrolo pyrrole type of compounds of chemical formulas (A), (B), (C), and (D):

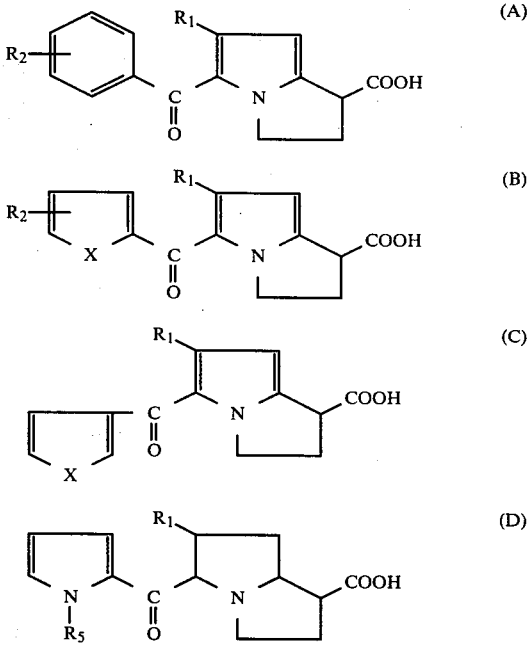

This invention also relates to a pharmaceutical composition for the treatment, inhibition and prevention of microvascular diseases which composition is comprised of pharmaceutically acceptable excipient in admixture with a therapeutically effective amount of a compound chosen from those represented by the formulas (A), (B), (C), and (D).

DETAILED DESCRIPTION OF THE INVENTION

Definitions

As used herein the "pharmaceutically acceptable non-toxic salt" derivatives of the compounds of formulas (A), (B), (C), (D), are those compounds wherein H of the COOH moiety is replaced by a positive ion such as for example sodium or is combined with a suitable amine. These salt derivatives are prepared as discussed hereinafter by reacting the acid of formula (A), (B), (C) or (D) with a suitable base.

The pharmaceutically acceptable non-toxic esters of formula (A), (B), (C) or (D) are those compounds wherein the OH of the COOH moiety is replaced by an alkoxy of 1 to 12 carbon atoms or an esterified glycerol. These are prepared as discussed hereafter by reacting an appropriate alcohol with the acid of formula (A), (B), (C) or (D).

The term "alkyl" refers to and includes branched and straight chain hydrocarbons containing the number of carbons indicated. Typical alkyl groups include methyl, ethyl, propyl, isopropyl, butyl, tertiary butyl, neopentyl, isopentyl, hexyl, octyl, nonyl, isodecyl, 6-methyldecyl.

The term "lower alkyl" means a branched or unbranched saturated hydrocarbon of 1-4 carbons, such as, for example, methyl, ethyl, n-propyl, i-butyl and the like.

The term "alkoxy" refers to a straight or branched chain alkyl ether group wherein "alkyl" is as defined above. This includes radicals such as methoxy, ethoxy, 2-propoxy, butoxy, 3-pentoxy and the like.

"Lower alkoxy" means the group —OR wherein R is lower alkyl as herein defined.

"Halo" as used herein means a halogen ion chosen from those of fluoro, iodo, bromo, or chloro.

"Aroyl" as used herein refers to the radical R—CO— wherein R is five or six carbon aromatic group. Exemplary compounds of aroyl are benzolyl, 2-furoyl, 2-thenoyl, 3-furoyl or 3-thenoyl and the like.

In naming the compounds of this invention IUPAC nomenclature is used. The substituents attached to the aromatic ring are identified by number of the carbon atom on the aromatic ring to which said substituent is attached according to the following scheme illustrations:

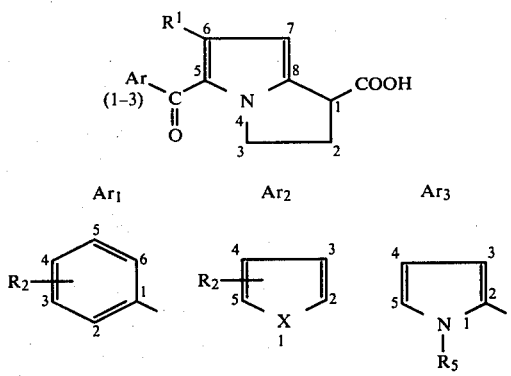

The $R_2$ substituent on the phenyl ring is at the ortho, meta or para positions, while the $R_2$ substituent on the furan or thiophene ring is at the 3, 4 or 5 position.

Preferred Embodiments

The broadest aspect of this invention is given in the "Summary of the Invention" in this specification. A preferred subgroup of compounds is represented by Formula (A), particularly those wherein $R_1$ is H or methyl and more particularly those where $R_2$ is H or methyl, methoxy, methylthio, or chloro at the para position.

Most preferred and exemplary compounds useful in the method of the present invention include, but are not limited to, 5-benzoyl-1,2-dihydro-3H-pyrrolo(1,2-a)-pyrrole-1-carboxylic acid, 5-(para-methylthio)benzoyl-1,2-dihydro-3H-pyrrolo(1,2-a)-pyrrole-1-carboxylic acid, 5-(para-methoxy)-benzoyl-1,2-dihydro-3H-pyrrolo(1,2-a)-pyrrole-1-carboxylic acid and individual (l-) and (d-) acid isomers thereof and the pharmaceutically acceptable nontoxic alkyl esters and salts.

Preparation Procedures

Detailed description of the preparation of 5-aroyl-1,2-dihydro-3H-pyrrolo[1,2-a]pyrrole-1-carboxylic acid compounds of Formula (A) and their pharmaceutically acceptable non-toxic esters and salts thereof is hereby incorporated by reference to the U.S. Pat. No. 4,089,969 to Muchowski et al, issued on May 16, 1978.

Detailed description of the preparation of 5-aroyl-6-chloro or 6-bromo-1,2-dihydro-3H-pyrrolo(1,2-a)-pyrrole-1-carboxylic acid compounds of Formula (B) and the pharmaceutically acceptable non-toxic esters and salts thereof is hereby incorporated by reference to the Patent Application No. 06/157,719, to Muchowski, allowed on Apr. 22, 1981, not issued as yet.

Detailed description of the preparation of 5-substituted-1,2-dihydro-3H-pyrrolo(1,2-a)pyrrole-1-carboxylic acid of Formulas (B) and (C) and the pharmaceutically acceptable non-toxic esters and salts thereof is hereby incorporated by reference to the U.S. Pat. No. 4,087,539 to Muchowski et al, issued in May 2, 1978.

Detailed description of the preparation of 5-(2-pyrroyl) and 5-(N-lower alkyl-2-pyrroyl)-1,2-dihydro-3H-pyrrolo[1,2-a]pyrrole-1-carboxylic acid compounds of Formula (D) and the pharmaceutically acceptable non-toxic esters and salts thereof is hereby incorporated by reference to the U.S. Pat. No. 4,097,579 to Muchowski et al, issued in June 27, 1978.

Detailed description of the preparation of 5-alkylsulfinylbenzoyl- and 5-alkylsulfonylbenzoyl-2-dihydro-3H-pyrrolo[1,2-a]pyrrole-1-carboxylic acid compounds of the Formula (A) and their pharmaceutically acceptable non-toxic esters and salts is hereby incorporated by reference to the U.S. Pat. No. 4,232,038 to Kluge et al, issued on Nov. 4, 1980.

5-Alkylthiobenzoyl-1,2-dihydro-3H-pyrrolo[1,2-a]pyrrole-1-carboxylic acid compounds of Formula (A) are prepared by a process illustrated by the following reaction sequence:

Reaction Sequence

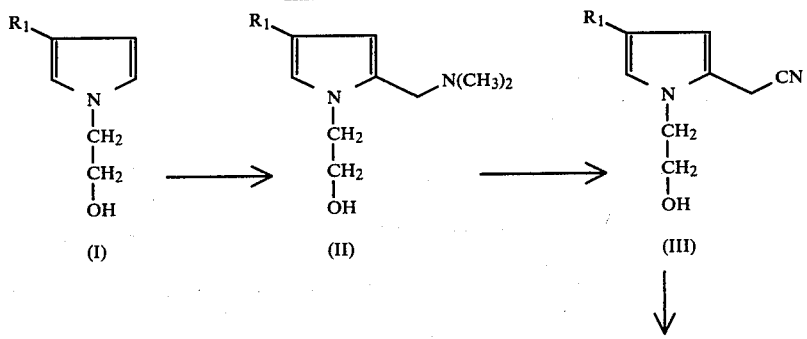

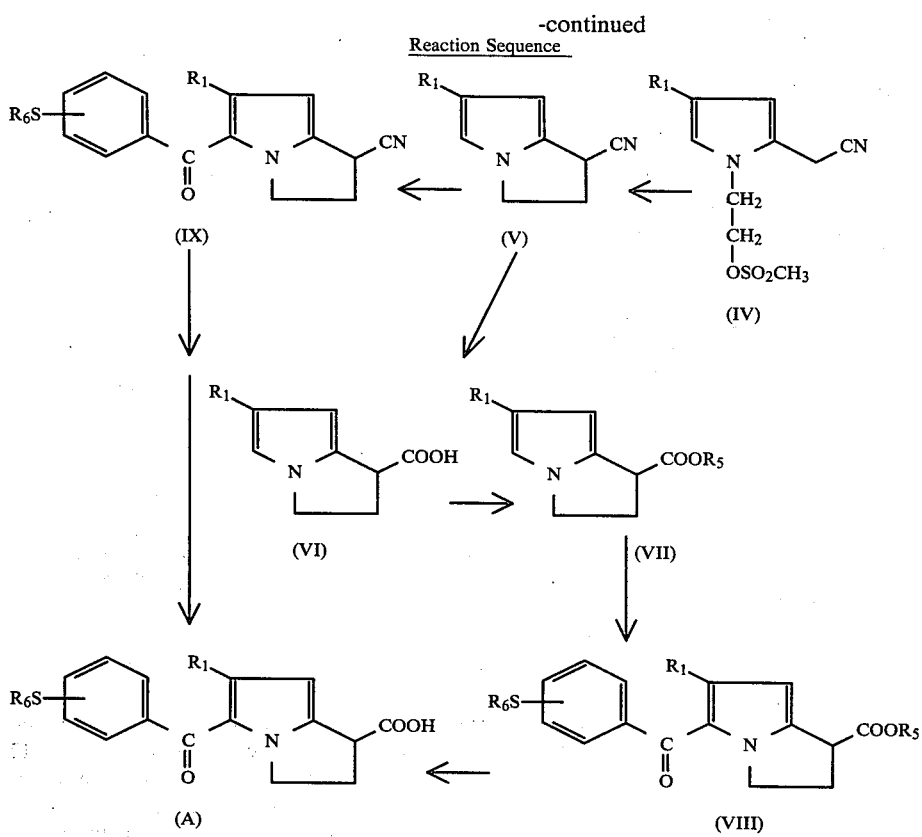

-continued
Reaction Sequence $R_1$ represents hydrogen; lower alkyl group having from one to four carbon atoms; chloro or bromo;

$R_5$ represents methyl, ethyl, isopropyl or n-butyl depending on whether methanol, ethanol, isopropanol or n-butanol are used for esterification;

$R_6$ represents alkyl;

The starting compound 2-aminoethanol acetate (not shown) is prepared by reacting 2-aminoethanol with glacial acetic acid at a temperature of between 5° and 50° C. This compound is then reacted with dimethoxytetrahydrofuran at reflux temperature for a period of time sufficient to give the desired pyrrole and the corresponding acetate. The reaction takes generally less than about 5 hours. After extracting the product from the reaction mixture, the mixture is hydrolyzed using a basic alcohol mixture such as sodium hydroxide and methanol at room temperature to give solely the desired product represented by formula (I).

This in turn is reacted at slightly elevated temperatures, e.g. 20°–60° C., with a solution of dimethylamine hydrochloride in aqueous formaldehyde to give 1-(2-hydroxyethyl)-2-dimethylaminomethylpyrrole (II). After extraction with a suitable organic solvent such as dichloromethane and subsequent purification by evaporation and distillation, the compound represented by Formula (II) is then dissolved in acetone and is maintained in an inert atmosphere using nitrogen or argon and a slight molar excess of dimethylsulfate is added to the cooled reaction mixture at such a rate that the temperature does not exceed about 5° C. When addition of the dimethylsulfate is completed, the solution is stirred at room temperature and a solution of sodium cyanide in water is added. The resulting reaction mixture is heated to reflux temperature, i.e. generally about 90°–100° C. and the distillate is collected. The reaction mixture is heated at gentle reflux for a suitable period of time, generally less than 2 hours, preferably about ½ hour and water is added to the mixture. After extracting, drying and purification by column chromatography, a nitrile represented by Formula (III) is obtained, namely 1-(2-hydroxyethyl)pyrrol-2-yl-acetonitrile.

The compound of Formula (III) is then converted to the corresponding 1-(2-methanesulfonyloxy)ethylpyrrol-2-yl-acetonitrile by esterification with methanesulfonyl chloride in the presence of a tertiary amine, i.e., triethylamine, pyridine and the like. Optionally, in the presence of a solvent such as dichloromethane, at a temperature from about −10° C. to about room temperature, for about 10 minutes to about 2 hours esterification produces the corresponding mesyl ester. The mesyl ester represented by Formula (IV) is converted to the corresponding 1-cyano-1,2-dihydro-3H-pyrrolo-[1,2-a]pyrrole of Formula (V). By reaction with sodium iodide in acetonitrile solution, at reflux temperature for from about 1 to about 10 hours. The preparation of the compound of Formula (V) is discussed in U.S. Pat. No. 4,100,698 to Van Horn et al and that patent is incorporated herein by reference.

Nitrile of Formula (V) can be converted into the acid represented by Formula (VI) by reacting with aqueous sodium or potassium hydroxide in ethylene glycol at elevated temperatures of up to 120° C. for a time sufficient for the reaction to take place, generally less than about 5 hours. Extracting the reaction mixture with a suitable organic solvent, bringing the aqueous phase to an acid pH by using concentrated hydrochloric acid and extracting from water, results in the acid represented by Formula (VI). The acid, in turn, is converted to the ester of Formula (VII) by reaction with a lower aliphatic alcohol in the presence of an acid such as hydrochloric acid.

The carboxylic acid group at the C-1 position in compound (VI) is selectively esterified by treatment with a lower aliphatic alcohol, e.g., methanol, ethanol, isopropanol, n-butanol and the like in the presence of hydrogen chloride, to produce the corresponding alkyl 1,2-dihydro-3H-pyrrolo[1,2-a]pyrrole-1-carboxylic acid of Formula (VII). The reaction is conducted at a temperature of from about 0° to about 50° C., for about 1 to about 4 hours.

A compound of Formula (VII) is then converted to the alkylthiobenzoyl compound of Formulas (VIII) and (A) by a condensation of a compound (VII) with either an acid chloride of the formula

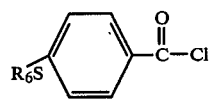

or a reagent prepared from an amide of the formula

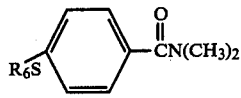

and phosphorus oxychloride wherein $R_6$ has the above-indicated meaning, affords the corresponding alkyl 5-benzoyl-1,2-dihydro-3H-pyrrolo[1,2-a]pyrrole-1-carboxylic acid (VIII). This is done following process conditions set forth in U.S. Pat. No. 4,089,969.

In the preferred embodiment of this process, this condensation is carried out by adding a solution of compound of Formula (VII) in a suitable solvent to a previously refluxed mixture of 1.1 to 5 molar equivalents of both the desired amide and phosphorus oxychloride in the same solvent, refluxing the reaction mixture thus obtained for from about 6 to about 72 hours under an argon atmosphere and thereafter adding thereto from about 3 to about 10 molar equivalents of sodium acetate, followed by an additional reflux period for from about 4 to about 6 hours.

Alternatively, the intermediate nitrile of Formula (V) can be converted into the nitrile of Formula (IX) in Reaction Scheme using reaction conditions discussed hereinbefore in the conversion of the compound of Formulas (VII) to (VIII). The compound of Formula (IX), in turn, is converted to a compound (A) of the invention by converting the nitrile moiety to an acid as discussed hereinbefore.

The compounds of Formula (A) can be resolved, according to methods known in the art, to obtain the corresponding individual isomers thereof.

The (l)-acid isomers and (d)-acid isomers of the compounds of Formula (A) can be obtained by applying the known technique of high pressure liquid chromotography (HPLC) to the α-phenethyl diastereoisomeric esters of the compounds of Formula (A), followed by acid cleavage. Thus, for example, the compounds of Formula (A) wherein $R_1$ and $R_6$ are both hydrogen can be subjected to further treatment in accordance with the following flow diagram:

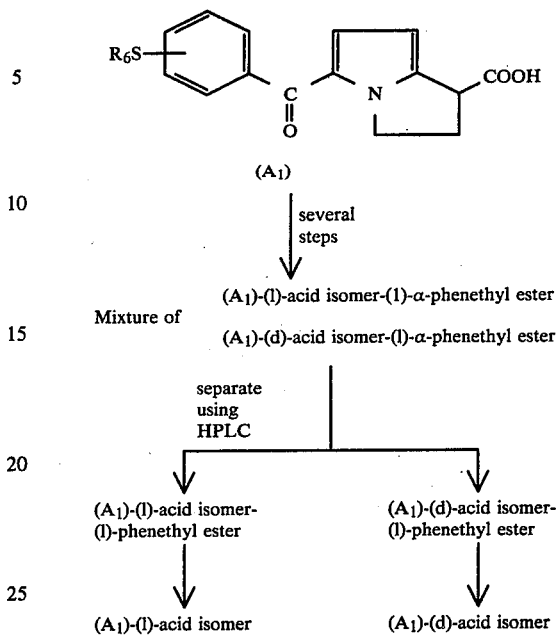

The free acids of Formula (A), (B), (C) and (D) can be converted into other alkyl esters having from 1 to 12 carbon atoms by conventional methods, e.g., by treatment with (a) the alcohol corresponding to the desired ester in the presence of a strong mineral acid, (b) an ethereal diazoalkane or (c) the desired alkyl iodide in the presence of lithium carbonate.

The salt derivatives of the compounds of Formula (A), (B), (C) and (D) are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopro-pylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, methylglucamine, theobromine, purine, piperazine, piperidine, N-ethyl-piperidine, polyamine resins and the like. The reaction is conducted in water, alone or in combination with an inert, water-miscible organic solvent, at a temperature of from about 0° to about 100° C., preferably at room temperature. Typical inert, water-miscible organic solvents include methanol, ethanol, isopropanol, butanol, acetone, dioxane or tetrahydrofuran. The molar ratio of compounds of Formula (A), (B), (C) and (D) to base used are chosen to provide the ratio desired for any particular salt. For preparing, for example, the calcium salts or magnesium salts of the compounds of Formula (A), (B), (C) and (D) the free acid starting material can be treated with at least one-half molar equivalent of pharmaceutically acceptable base to yield a neutral salt. When the aluminum salts of the compounds of Formula (A), (B), (C) and (D) are prepared, at least one-third molar equivalent of the pharmaceutically acceptable base are employed if a neutral salt product is desired.

In the preferred procedure, the calcium salts and magnesium salts of the compounds of Formula (A), (B), (C) and (D) can be prepared by treating the corresponding sodium or potassium salts thereof with at least one-half molar equivalent of calcium chloride or magnesium chloride, respectively, in an aqueous solution, alone or in combination with an inert water-miscible organic solvent, at a temperature of from about 20° to about 100° C. Preferably, the aluminum salts of the compounds hereof, can be prepared by treating the corresponding free acids with at least one-third molar equivalent of an aluminum alkoxide, such as aluminum triethoxide, aluminum tripropoxide and the like, in a hydrocarbon solvent, such as benzene, xylene, cyclohexane and the like, at a temperature of from about 20° to about 115° C. Similar procedures can be used to prepare salts of inorganic bases which are not sufficiently soluble for easy reaction.

The salt derivatives of the compounds of formula (A), (B), (C) and (D) can be reconverted to their respective free acids by acidifying said salts with an acid, preferably an inorganic acid, e.g., hydrochloric acid, sulfuric acid, and the like, at temperature of from about 0° C. to about 50° C., preferably at room temperature.

The pharmaceutically acceptable non-toxic esters of formula (A), (B), (C) and (D) are prepared by esterifying the corresponding free acids with an alcohol reagent corresponding to the desired ester, e.g., an alkanol having up to 12 carbon atoms or with glycerol which is already esterified at two hydroxyls to other suitable acids. This reaction is conducted in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in an inert organic solvent in which the free acids and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichlorethane; or an ether solvent, e.g., diethyl ether, dibutyl ether dioxane, tetrahydrofuran, and the like. In the case where the alcohol reagent is a solid, the reaction preferably is conducted in a non-aqueous liquid inert organic solvent. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

Typical esters are those ester derivatives prepared from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by the transesterification to the ethyl ester.

It is to be understood that isolation of the compounds described herein can be effected, if desired, by any suitable separation or purification procedure, such as for example, extraction, filtration, evaporation, distillation, crystallization, thin-layer chromatography or column chromatography, high pressure liquid chromotography (HPLC) or a combination of these procedures.

The novel compounds of Formula (A), (B), (C) and (D) depicted above exist as pairs of optical isomers (or enantiomorphs), i.e., a (dl) mixture. However, each optical isomer as well as the (dl) mixtures thereof are included within the present invention.

While the (d)-acid isomers are not used as a medicinal of agents per se, they can, if desired, be converted to their pharmaceutically acceptable, nontoxic esters and salts thereof according to the methods described for the conversion of the (l-)acid isomers to their pharmaceutically acceptable, nontoxic esters and salts thereof.

Utility and Administration

This invention is directed to a method useful for relieving, inhibiting or preventing microvascular diseases associated with diabetes mellitus in mammals. These diseases may be, among others, diseases of the retina, diseases of the skin, diseases of the kidney, or peripheral, central or autonomic nervous system. All these may, and often occur, as symptoms associated with the acute or chronic complications of diabetes mellitus such as initial leakage from the capillaries to the extracellular space in acute form of diabetes up to such chronical complications as diabetic retinopathy, diabetic nephropathy or diabetic neuropathy.

The method of this invention is both curative and preventative. While not intending to be bound by any theoretical mechanisms of action, the method herein is believed to prevent the changes in the permeability of the vascular wall, thus preventing the leakage from the vascular wall into the extracellular space and thus preventing the damage to the vascular system which would otherwise be caused by such leakage. Moreover, the method also operates to prevent neovascularization, the formation of new capillaries or blood vessels in the later stages of disease. While the preventative action of the claimed compounds affects the stages prior to development of serious complications of diabetes mellitus, the secondary action brings relief to the patients with diabetes where chronical complications are in advanced stage and well developed. The administration of these compounds during the chronic disease inhibits further deterioration of microvascular system and development of microvascular diseases associated with diabetes. The method is useful in treatment of a mammal, particularly a human being, having diabetes mellitus, whether the patient already exhibits the symptoms or whether the symptoms are not as yet detectable.

The compounds of this invention and their pharmaceutically acceptable non-toxic alkyl esters and salts have been found, in animal experiments, to have a profound effect on development and prevention of microvascular diseases when administered systemically to the animal with experimentally induced microvascular disease. These compounds are highly potent in preventing the development of neovascularization during diabetic retinopathy, or in preventing the leakage from the blood vessels into the vitreous humor which is characteristic of various microvascular diseases.

In the practice of the method of the present invention, an effective amount of compounds of the present invention or pharmaceutical compositions thereof, as defined above, are administered via any of the usual and acceptable methods known in the art, either singly or in combination with another compound or compounds of the present invention or other pharmaceutical agents, such as antibiotics, hormonal agents for the treatment of microvascular diseases such as insulin and so forth. These compounds or compositions can be administered orally, topically, parenterally, or by inhalation and in the form of either solid, liquid, or gaseous dosage including tablets, suspensions, and aerosols. However, it should be noted that the method of administering the active ingredients of the present invention is not considered as limited to any particular mode of administration. The administration can be conducted in single unit dosage form with continuous therapy or in single dose therapy ad libitum. Other modes of administration are effective for treating the conditions of retinopathy, nephropathy or neuropathy. In the preferred embodiments, the method of the present invention is practiced when relief of symptoms is specifically required, or, perhaps, imminent. The method hereof may also be usefully practiced as a continuous or prophylactic treatment.

In view of the foregoing as well as in consideration of the degree of severity of the condition being treated, age of subject, body weight, and so forth, all of which factors being routinely determinable by one skilled in the art, the effective dosage in accordance herewith can vary over a wide range. Generally, an effective amount ranges from about 0.005 to about 50 mg/kg/body weight/day and preferably from about 0.01 to about 20 mg/kg/body weight/day. In alternate terms, an effective amount in accordance herewith generally ranges from about 0.175 to about 3500 mg/day/subject weighing 70 kg, preferably about 3 to 700 mg. Of course, the dosage of each compound is given in accordance with the range designated on the label of the formulated drug where known and otherwise in accordance with good medical practices. In essence, in accordance with the invention the compounds can be administered for the treatment of microvascular diseases in essentially the same amounts as being administered for the treatment of inflammatory conditions, or conditions where treatment with an analgesic is indicated.

Useful pharmaceutical carriers employed for the preparation of the compositions hereof, can be solids, liquids, or gases. Thus, the compositions can take the form of tablets, pills, capsules, powders, sustained release formulations, solutions, suspensions, elixirs, aerosols, and the like. The carrier can be selected from the various oils including those of petroleum, animal, vegetable or synthetic origin, or example, peanut oil, soybean oil, mineral oil, sesame oil, and the like. Water, saline, aqueous dextrose and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glyceryl monostearate, sodium chloride, dried skim milk, glycerol, propylene glycol, water, ethanol, and the like. Suitable pharmaceutical carriers and their formulation are described in *Remington's Pharmaceutical Sciences,* Easton, Pa., Mack Publishing Company, Fifteenth Ed., 1975. Such compositions will, in any event, contain an effective amount of the active compound together with a suitable amount of carrier so as to prepare the proper dosage form for proper administration to the host. Generally, the active ingredient will be present in an amount of about 0.1% to 99% by weight, preferably 5 to 75% by weight while the pharmaceutical excipients will be present in an amount of about 99.9% to about 1% by weight, preferably about 95 to about 25% by weight.

A more recently devised approach for parenteral administration employs the implantation of a slow-release or sustained-release system, such that a constant level of dosage is maintained. See, e.g., U.S. Pat. No. 3,710,795.

The following examples are given to indicate how to determine the initial activity of the compounds which were useful in the method of this invention and to set forth useful formulations. The examples are given as representative only and are not to be construed as limiting the scope of the invention to only the use of the compounds which are disclosed therein.

EXAMPLE 1

It has been found in clinical studies of diabetic human patients that prior to any visible change in the retinal blood vessels, there is leakage from the blood vessels into the vitreous humor. This can be demonstrated by injecting fluorescein into the blood stream of the patient, then monitoring the vitreous humor for the presence of fluorescein. The amount of fluorescein present in the vitreous humor can then be determined by vitreous fluorophotometry as described by Cunha-Vaz et al (Brit. J. Ophthal 59:649–656, 1975).

This same phenomenon can be seen in diabetic laboratory rats. Thus, rats are used in this experiment to determine the effect of active compounds on diabetic retinopathy.

Forty male Long-Evans rats (200–250 grams) are divided into three groups of ten each. Two of the three groups receive streptozotocin (65 mg. per kg.) intravenously to induce diabetes. The remaining group receives only the vehicle (a citrate buffer) and serves as the control group. The three groups are as follows:

| Group No. | Diet |
|---|---|
| I-Control | Purina Lab Chow |
| II-Diabetic | Purina Lab Chow |
| III-Diabetic/Active Compound | 0.05% Active Compound in Purina Lab Chow |

Each group remains on the above diet for three weeks. The rats in group III ingest about 10 mg of Active Compound per day. After three weeks, each rat receives fluorescein (10 mg/kg) and is sacrificed one hour later. A blood sample is taken by cardiac puncture at the time of sacrifice. The eyes are removed and frozen in dry ice/isopropanol bath. The vitreous humor is extracted while the eye is frozen and each sample is weighed and dissolved in 1 ml. of 0.1 normal sodium hydroxide. The fluorescein content is determined fluorometrically at 460 nanometers (nm) excitation and 510 nm emission wavelengths. Fluorescence readings are converted into units of fluorescein (nanograms ng) by the use of a standard curve. Plasma fluorescein is also determined and expressed as micrograms ($\mu$g) fluorescein per ml of plasma. Results are expressed as leakage which is defined as:

$$\text{Leakage} = \frac{\text{ng fluorescein per gram vitreous}}{\mu\text{g fluorescein per ml plasma}}.$$

Thus, the higher the leakage value, the greater the ratio of fluorescein in the vitreous compared with the amount present in plasma. This indicates that the fluorescein could get into the vitreous humor readily by breakdown of the blood-retinal barrier and by leakage of fluorescein through microvessels.

Plasma glucose is determined in all groups to confirm that animals are actually diabetic in the diabetic groups. Glucose is determined by specific hexokinase enzymatic method specific for glucose.

Active compounds of this invention are able to prevent the increase in leakage associated with diabetes.

EXAMPLE 2

| Ingredients | Quantity per tablet, mg. |
|---|---|
| 5-benzoyl-1,2-dihydro-3H—pyrrolo(1,2-a)-pyrrole-1-carboxylic acid | 250 |
| cornstarch | 50 |
| lactose | 198 |
| Magnesium stearate | 2 |

EXAMPLE 3

| Ingredients | Quantity per tablet, mg. |
|---|---|
| 5-(para-methylthio)benzoyl-1,2-dihydro-3H—pyrrolo-(1,2-a)-pyrrole-1-carboxylic acid | 250 |
| cornstarch | 50 |
| lactose | 198 |
| Magnesium stearate | 2 |

EXAMPLE 4

| Ingredients | Quantity per tablet, mg. |
|---|---|
| 5-(para-methoxy)-benzoyl-1,2-dihydro-3H—pyrrolo-(1,2-a)-pyrrole-1-carboxylic acid | 250 |
| cornstarch | 50 |
| lactose | 198 |
| Magnesium stearate | 2 |

The above ingredients are mixed intimately in the above ratios and pressed into single scored tablets.

EXAMPLE 5

An intimate mixture is prepared of equal parts of 5-benzoyl-1,2-dihydro-3H-pyrrolo(1,2-a)-pyrrole-1-carboxylic acid and a tablet base comprising starch with the addition of 1% magnesium stearate as a lubricant. The mixture is compressed into tablets containing 400 mg of active compound.

EXAMPLE 6

An intimate mixture is prepared of equal parts of 5-(para-methylthio)benzoyl-1,2-dihydro-3H-pyrrolo(1,2-a)-pyrrole-1-carboxylic acid, and a tablet base comprising starch with the addition of 1% magnesium stearate as a lubricant. The mixture is compressed into tablets containing 400 mg of active compound.

EXAMPLE 7

An intimate mixture is prepared of equal parts of 5-(para-methoxy)-benzoyl-1,2-dihydro-3H-pyrrolo(1,2-a)-pyrrole-1-carboxylic acid and a tablet base comprising starch with the addition of 1% magnesium stearate as a lubricant. The mixture is compressed into tablets containing 400 mg of active compound.

EXAMPLE 8

An intimate mixture is prepared of 50 parts 5-benzoyl-1,2-dihydro-3H-pyrrolo(1,2-a)-pyrrole-1-carboxylic acid, 149 parts cornstarch and 1 part magnesium stearate. The mixture is placed in capsules containing 50 mg active ingredient.

EXAMPLE 9

An intimate mixture is prepared of 50 parts 5-(para-methylthio)benzoyl-1,2-dihydro-3H-pyrrolo(1,2-a)-pyrrole-1-carboxylic acid, 149 parts cornstarch and 1 part magnesium stearate. The mixture is placed in capsules containing 50 mg active ingredient.

EXAMPLE 10

An intimate mixture is prepared of 50 parts 5-(para-methoxy)-benzoyl-1,2-dihydro-3H-pyrrolo(1,2-a)-pyrrole-1-carboxylic acid, 149 parts cornstarch and 1 part magnesium stearate. The mixture is placed in capsules containing 50 mg active ingredient.

What is claimed is:

1. A method for inhibiting or relieving diabetic retinopathy, diabetic neuropathy and diabetic nephropathy in mammals which method comprises administering systemically to a mammal in need thereof a therapeutically effective amount of a compound of the formula:

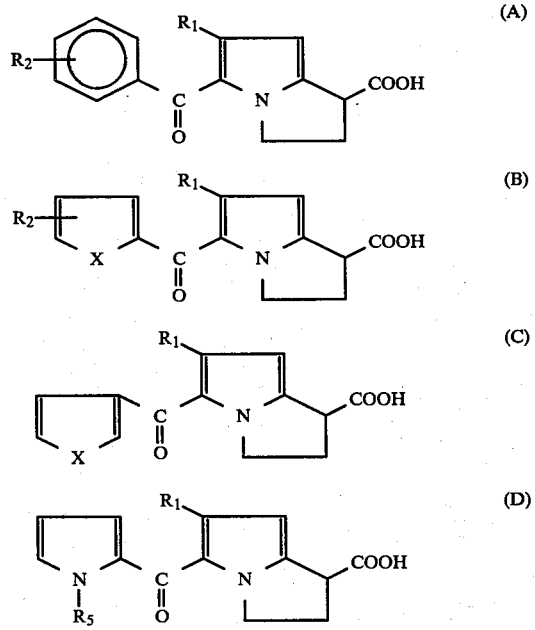

and the individual (l-) and (d-)acid isomers thereof and the pharmaceutically acceptable non-toxic esters and salts thereof, wherein $R_1$ represents hydrogen; lower alkyl group having from one to four carbon atoms; chloro or bromo;

$R_2$ represents hydrogen, a lower alkyl group having from one to four carbon atoms, a lower alkoxy group having from one to four carbon atoms, chloro, bromo, fluoro; or $R_4S(O)n$ wherein
  $R_4$ is lower alkyl and
  n is the integer 0, 1 or 2;

X represents oxygen or sulphur; and $R_5$ represents hydrogen or lower alkyl group having from one to four carbon atoms.

2. The method of claim 1 wherein compounds are represented by those of Formula (A).

3. The method of claim 2 wherein $R_1$ is hydrogen.

4. The method of claim 2 wherein $R_2$ is hydrogen, namely 5-benzoyl-1,2-dihydro-3H-pyrrolo[1,2-a]pyrrole-1-carboxylic acid.

5. The method of claim 2 wherein $R_2$ is $R_4S$ where $R_4$ is methyl and the $R_2$ substituent is at the para-position of the phenyl ring, namely 5-(p-methylthio)-benzoyl-1,2-dihydro-3H-pyrrolo[1,2-a]-pyrrole-1-carboxylic acid.

6. The method of claim 2 wherein $R_2$ is methoxy at the para-position, namely 5-(p-methoxy)-benzoyl-1,2-dihydro-3H-pyrrolo-[1,2-a]pyrrole-1-carboxylic acid.

7. The method of claim 2 wherein $R_1$ is methyl.

8. The method of claim 2 for inhibiting or relieving diabetic retinopathy.

9. The method of claim 2 for inhibiting or relieving diabetic nephropathy.

10. The method of claim 2 for inhibiting or relieving diabetic neuropathy.

* * * * *